Kamen

[11] Patent Number: 4,634,426
[45] Date of Patent: Jan. 6, 1987

[54] MEDICAL INFUSION CONTROLLER AND USER INTERFACE

[75] Inventor: Dean L. Kamen, Bedford, N.H.

[73] Assignee: Baxter Travenol Laboratories, Deerfield, Ill.

[21] Appl. No.: 680,500

[22] Filed: Dec. 11, 1984

[51] Int. Cl.4 ............................................. A61M 5/00
[52] U.S. Cl. ............................. 604/65; 128/DIG. 13
[58] Field of Search ................. 128/DIG. 13; 604/65, 604/66, 67, 251, 253; 73/861.41; 222/420, 422; 250/560

[56] References Cited

U.S. PATENT DOCUMENTS

| 4,321,461 | 3/1982 | Walker et al. | 604/65 X |
| 4,411,649 | 10/1983 | Kamen | 604/65 |
| 4,460,358 | 7/1984 | Somerville et al. | 128/DIG. 13 X |
| 4,481,827 | 11/1984 | Bilstad et al. | 604/65 X |
| 4,507,112 | 3/1985 | Hillel et al. | 128/DIG. 13 X |
| 4,525,163 | 6/1985 | Slavik et al. | 128/DIG. 13 X |

Primary Examiner—Edward M. Coven
Attorney, Agent, or Firm—Bromberg, Sunstein & McGregor

[57] ABSTRACT

An intravenous flow control system includes a programmed microprocessor which receives information from a drop sensor and varies the adjustment of a clamp to control the infusion rate. The system accepts total dose and infusion duration, or dose rate and time information keyed in by the user, and periodically develops a target rate, based on the amount of infusate already delivered, such target rate being calculated to correct the actual delivered dose to that determined by the user keyed data. The target rate differs from the programmed rate by an amount equal to the programmed rate times an adjustment factor. In a preferred embodiment a series of tolerance bands corresponding to delivered volume errors are defined, with the adjustment factor a constant in each tolerance band. For high rate discrepancies, slewing is used to correct the clamp adjustment. Inability to attain the target rate before the delivery of a threshold volume of fluid triggers an alarm. Further alarms are provided for high and low drip rates, streaming, and for deviation of the total volume outside of a progressively defined maximum tolerance band. Control rate and time data are entered by the user through a menu-driven keyboard, in response to displayed messages, thus requiring only INCREASE, DECREASE and SELECT keys.

14 Claims, 10 Drawing Figures

MAXIUN ALLOWED TOLLERANCE BAND

```
IF START UP
  THEN:
    MAX. BAND = 4
IF RATE ESTABLISHED
  THEN:
    IF 1ML DELIVERED
      THEN:
        IF MAX. BAND  1
          THEN:
            IF QCNT = 2
              THEN:
                MAX BAND = 4
              THEN:
                         ZERO ERROR
            ELSE:        MAX BAND = 2
           MAX. BAND - 1
```

TABLE II MAXBAND

IF CORRECTION FACTOR > 1 (UNDER DELIVERY)
  THEN:
    TARGET RATE = PROG. RATE + (PROG. RATE = R)
        (NOT TOO EXCEED 320 DROP/MIN)
IF CORRECTION FACTOR < 1 (OVER DELIVERY)
  THEN:
    TARGET RATE = PROG. RATE - (PROG. RATE = R)

IF ACTUAL VOLUME <> 2.5% OF IDEAL VOLUME
  THEN:
    TOLLERANCE BAND = 0
    K = 0%

IF ACTUAL VOLUME <> 5% OF IDEAL VOLUME
  THEN:
    TOLLERANCE BAND = 1
    K = 5%

IF ACTUAL VOLUME <> 10% OF IDEAL VOLUME
  THEN:
    TOLLERANCE BAND = 2
    K = 10%

IF ACTUAL VOLUME <> 25% OF IDEAL VOLUME
  THEN:
    TOLLERANCE BAND = 3
    K = 25%

IF ACTUAL VOLUME <> 50% OF IDEAL VOLUME
  THEN:
    TOLLERANCE BAND = 4
    K = 50%

TABLE I

MEDICAL INFUSION CONTROLLER AND USER INTERFACE

DESCRIPTION

Technical Field

The present invention relates to automated medical infusion systems, and in particular to such systems in which a user can enter dose and time data on a controller, which then operates to achieve the selected dosage by adjusting a clamp to control the flow of infusate to the patient. A number of such systems are known, which operate to maintain a preselected drip rate, or to terminate flow after a preselected volume has been delivered. One approach is to induce drop formation by actuating a vibrating drop former at predetermined intervals. Another approach is to determine the present drip rate, and, if it varies from the predetermined rate, to incrementally actuate a clamp, on the exit flow tube of the system, in a direction to cause the drip rate to match the predetermined rate. One difficulty with such rate correcting control systems is that the adjustment of a clamp to achieve a predetermined rate always results in some volume delivery error, and the cumulation of these errors over time may result in a large discrepancy in total volume delivered. In particular, in the commonly occurring event that the infusion tube to the patient is pinched off, the flow rate may drop to zero; upon resumption of flow, the subsequent adjustment to the preselected rate will do nothing to compensate for the missed period. Present systems simply actuate an occlusion alarm in such instances, and leave it to the attendant to make a dosage correction. Present systems also tend to have user interfaces that permit entry of fluid delivery parameters in non-sequential fashion and such parameters may be outside a range of values known to be within limits of established practice.

SUMMARY OF THE INVENTION

These and other drawbacks of prior infusion control systems are resolved in the present invention, in which a controller for a drip-type medical infusion system includes a microprocessor and a keyboard for user entry of dose and time data. In a preferred embodiment, the controller receives signals from a drip detector and continually monitors both the current drip rate and the total number of drops delivered. Based on the total drops delivered, a target rate is derived which will result in the delivery of the correct prescribed volume, and if this target rate differs from the current drip rate, the controller initiates a series of corrective clamp adjustments to attain the target rate. In a preferred embodiment, a hardware streaming detector actuates an alarm, and additional alarms, which are preferably realized in the control program of the microprocessor, indicate extreme high or low flow rates. In a preferred embodiment, long term alarms indicate certain states indicative of failure to achieve necessary volumetric tolerances, and another alarm is actuated in the event the target rate cannot be attained before delivery of a preset interim threshold volume. The user interface in accordance with a preferred embodiment displays only values for entry thereof that are within predetermined limits

DETAILED DESCRIPTION OF INVENTION

Figure 1:
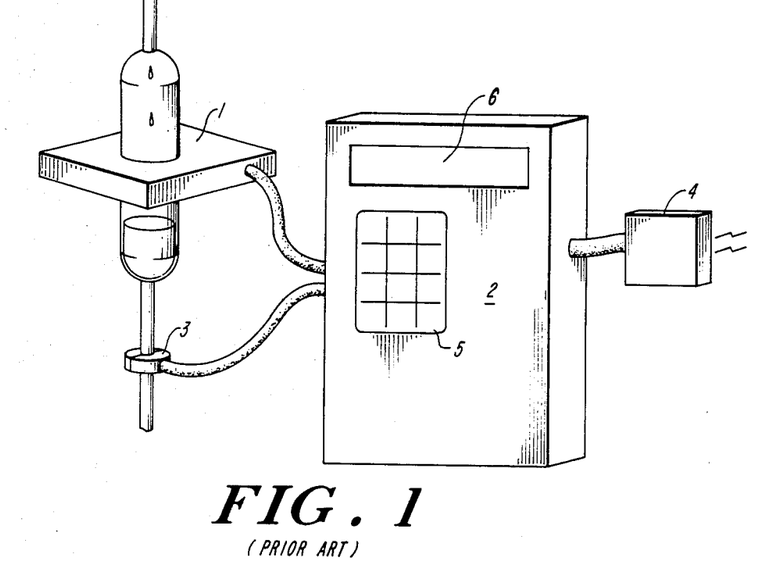
FIG. 1 shows in schematic form a prior art fluid delivery system.

Shown in FIG. 1 is a schematic of a typical prior art infusion control system, including a drip detector 1 surrounding a drip chamber with fluid inlet and outlet tubes; a controller 2 which may be set to a desired drip rate; a clamp 3 about the outlet tube controlled by the controller; and an alarm 4. In general, the drip rate will depend on the degree of clamp restriction of the outlet tube, so that controller 2 may maintain a desired rate by receiving drop detection signals from the detector, comparing the occurrence of such signals with its programmed drop rate, and actuating the clamp 3 in a manner to open or close it if the drip rate is, respectively, lower or higher than the programmed rate. Such a device may save a good deal of an attendant's time which would otherwise be spent manually readjusting the clamp and observing it for a sufficient period to verify a stable and desired level of flow.

Figure 3:
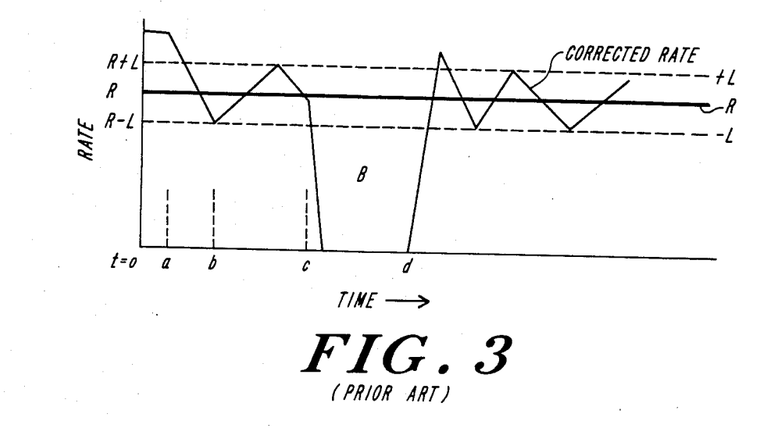
FIGS. 3 and 3A show a rate graph of a prior art rate control system, and the delivered volume of such system.
Figure 3A:
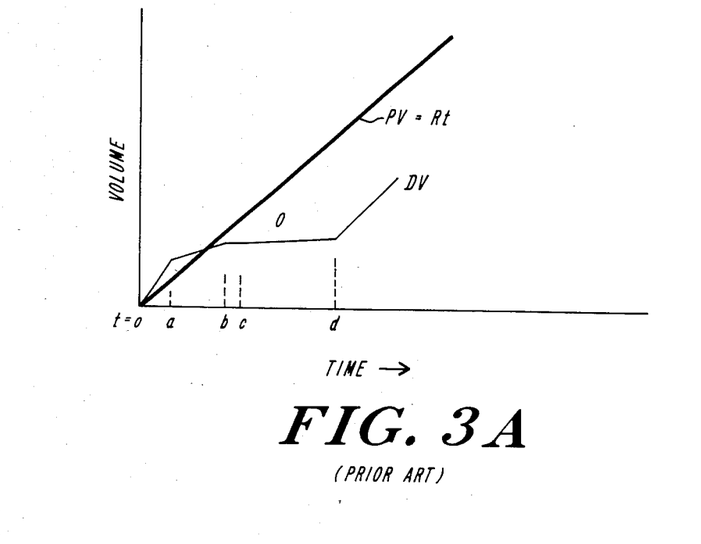

The quantitative operation of such a prior art system is shown graphically in FIGS. 3 and 3A. FIG. 3 shows an illustrative graph of the actual delivery rate of a prior art system which has been set to maintain a programmed drip rate "R," by controlling a clamp to modify the actual drip rate whenever it differs from R by an amount greater than a tolerance limit L. The drip rate, typically in drops per minute, is plotted on the vertical axis, and the time plotted on the horizontal axis. Initiation of infusion is, for purposes of illustration, taken as $t=o$. In the example shown, initially flow is somewhat above the programmed rate, and, accordingly, at time $t=a$ the controller closes down the clamp, resulting in a fairly quick decrease of flow rate. In this example, the rate overshoots, attaining lower limit $R-L$ at time $t=b$, whereupon the controller opens up the clamp, causing the rate to rise. The clamp adjustments continue whenever the rate goes outside the limits $R\pm L$, until, at time $t=c$, the flow rate abruptly falls to O, as may happen, for instance, when the flow tubing becomes pinched. In a typical system of this type, such event would result in the controller's opening the clamp, and possibly also activating an alarm. Thereafter, until time $t=d$ when the tube by chance or human intervention becomes deconstricted, no fluid is delivered. When the tube is freed up at $t=d$, the rate shoots up toward the programmed rate R, and, as before, may overshoot to $R+L$ whereupon a corrective clamp adjustment again occurs. It may be seen that the overall control of such a device results in a rate which oscillates above and below a fixed programmed rate, except when occluded.

The net effect of such a rate control process on delivered volume is plotted in FIG. 3A. The programmed volume, PV, corresponding to the constant delivery rate R, is a straight line of slope R. The actual delivered volume for the rate shown in FIG. 3 is shown by curve DV, which commences by accumulating at a rate larger than the programmed volume. When the tube is occluded, no change in delivered volume occurs for the duration of the occlusion, marked as "o" on the DV curve, and, as the occlusion continues, the actual volume thus ultimately falls below the programmed volume. Thereafter when flow resumes, current volume delivery occurs at a rate near to the ideal rate, but does not, except on a random basis, regain the volume lost during occlusion. If this deficit ("B" in FIG. 3) is large compared to the overshoot fluctuations of the rate controller, the occlusion volume deficit remains throughout the subsequent delivery, and may, alone or in conjunction with later occlusion deficits, result in a substantial error in total delivered dose.

Figure 2:
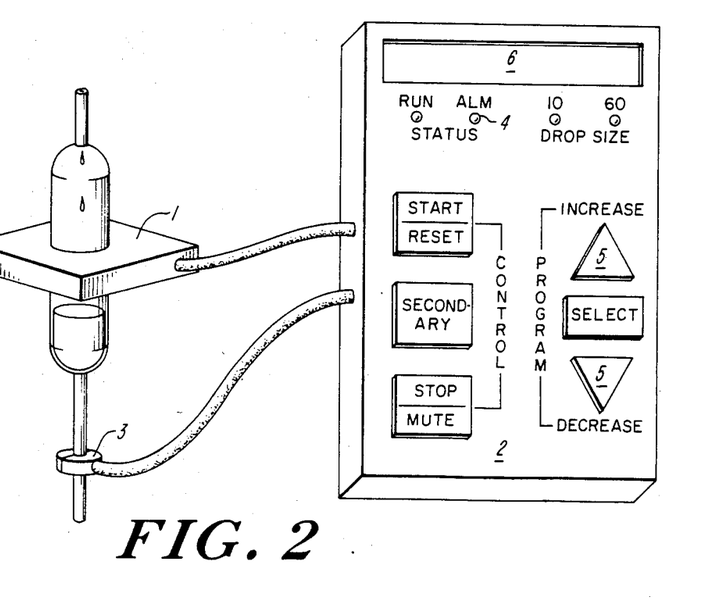
FIG. 2 shows a schematic view of the components of the present invention.

Turning now to FIG. 2, there is shown a schematic of the infusion control system of my invention, having a detector 1, controller 2, alarm 4 and a clamp 3 controlled by the controller. The controller 2 has a data entry means, which, in the preferred embodiment, includes a number of keys 5 by which a user responding to prompting messages on display 6, may enter desired dose and time information. The display 6, which may be, for example, a liquid crystal or a gallium arsenide display, is used to display user data entry and set-up instructions, stored data and alarm warnings, and corrective instructions to the user.

Controller 2 contains a microprocessor, which operates under the control of an instruction program embedded in a read-only memory, and also contains a read-write memory for the storage and manipulation of data, in a manner well understood in the art. As discussed more fully below, the operation of controller 2 is initiated by a user interacting with prompting messages on the display to key in data such as the total dose, starting and stopping infusion times, type of set, or other data adequate to specify or derive the rate(s) and time(s) of infusion. Thereafter the controller receives a signal from the detector each time a drop falls, and, operating under the control of its stored program, generates corrective signals to modify the adjustment of clamp 3, and also develops signals to drive the display 6 so as to display the current rate and volume data derived from the detector signals. The present controller is preferably used to control a clamp such as those shown in my co-pending applications Ser. Nos. 479,328 and 551,956, filed on Mar. 28, 1983 and Nov. 11, 1983, respectively, which applications are incorporated herein by reference. Such clamps, which may be conveniently driven in small incremental or continuous amounts in either an opening or closing direction, and which maintain a stable rate of flow between changes in adjustment, are suited to the iterative control and adjustment regimen of the present controller, further described below Controller 2 includes a first microprocessor for implementing its rate control program and also a second microprocessor, which, in a manner understood in the computer art, is configured as a slave which periodically swaps stored data indicative of all current states and calculations and checks it against that of the first microprocessor. The slave serves a fail-safe function of checking all accumulated data and program steps, and also serves to drive certain safety alarms, and provide additional input/output capabilities for the controller. The architecture of the controller is set forth in FIG. 8.

Figure 8:
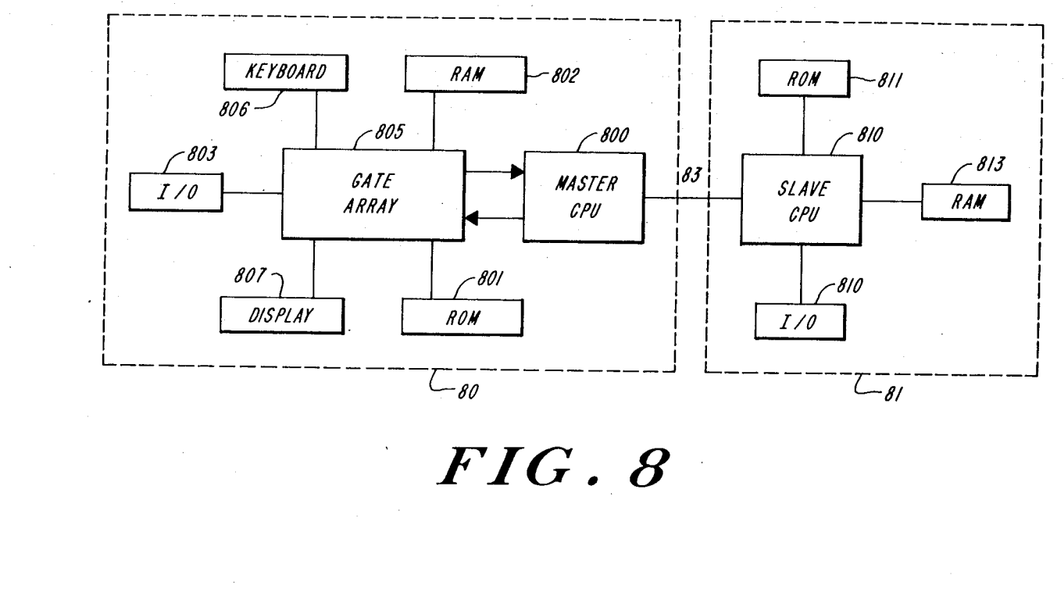
FIG. 8 shows a block diagram of the controller architecture of a preferred embodiment.

Turning now to FIG. 8 there is shown the architecture of the controller 2 comprising a primary, or master processing section 80 and a slave or backup section 81. Slave section 81 comprises a microprocessor 810, which in a prototype embodiment is an 8051 chip, as well as a ROM 811 in which a set of operating instructions for the microprocessor are written, and a RAM 812 for the storage and retrieval of data. Slave section 81 also includes a number of input/output lines 813; the input lines may include for instance a line for receiving signals indicative of a falling drop from a drip detector. The output lines may include, for instance lines for actuating various alarms, and for delivering suitably encoded information to drive the alphanumeric display. Master processing system 80 also includes a microprocessor 800, a ROM 801, a RAM 802, and an input/output section 803. However these latter elements communicate with the master microprocessor 801 via a gate array 805 which, in addition, is connected to a keyboard 806 and display 807. As shown, the gate array receives signals from the master processor 801 so as, at given time to enable information to flow to or from one or the other of the keyboard 800, display 807, RAM 802, ROM 801 or input/output lines 803. In addition, a communications link 83 allows data to flow directly from the master processor 801 to the slave processor 811. During the master slave operation of the controller, all data in the RAM and all instructions of the control program are checked against each other every minute, and in the event that the two sections of the controller fail to agree, an alarm is sounded and appropriate warning messages displayed on the display 807.

One aspect of the present invention which is considered a distinct improvement over prior art infusion controllers is the manner in which the present invention accommodates data entry. When the start button is first pressed to turn the controller on, a prompting message which may be read directly from the ROM is displayed on display 807, to alert the user that the next keyboard entry will set the infusion rate (or duration). In the preferred embodiment shown, the keyboard comprises INCREASE, DECREASE, and SELECT keys, rather than a complete numeric keyboard. Following the prompt on the display, the user need only push seriatim the INCREASE and/or DECREASE keys until the desired rate is displayed on the display 807. The INCREASE or DECREASE keys thus will cause the display in effect to scroll up or down respectively through a preset range of numbers or a predetermined set of other possible types of entries. This approach permits a generalized system for entry of all types of data. This approach neatly avoids the problem of entry of any data outside permissible limits, by displaying and allowing the selection only of permissible values. Moreover, the resolution for numeric entries can be tailor-made for each parameter being entered. Two additional advantages of this mode of data entry are that it permits a simplified keyboard, and that it requires the user to consciously perform each step of the setting up serially. If there is a wide range to be covered, the system can be designed, for example, so that first pressing the INCREASE or DECREASE key causes slow scrolling and, after holding it depressed for a predetermined period causes fast scrolling; dual speed scrolling will permit converging rapidly on a desired value and thereafter achieving precision in the final selection by slower scrolling. When the display finally indicates the desired value or entry, the selection thereof as an operating parameter is accomplished simply by pushing the SELECT key.

After the dosage rate or duration is set, the gate array 805 connects the display 807 to receive a second prompting message from CPU 800 or 810 to alert the user to set the time. The keyboard and display are then connected, via array 805, for the user to enter the time interval over which the dosage is to be delivered. Further prompting messages may be provided to indicate the set being used, to have the user confirm the dosage data entered, and to display any necessary warnings indicative, e.g., that the clamp or drip detector is not properly attached. It is believed that the use of a menu driven keyboard of the type herein described for entering user determined dosage and time data provides a new and significant advance in the art of medical infusion technology.

Figure 6:
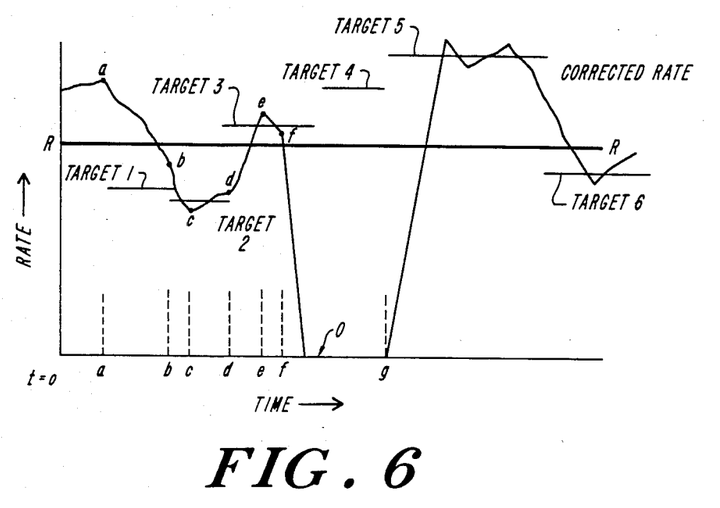
FIG. 6 and 6A show graphs of the rate control of the present invention, and the delivered volume, respectively.
Figure 6A:
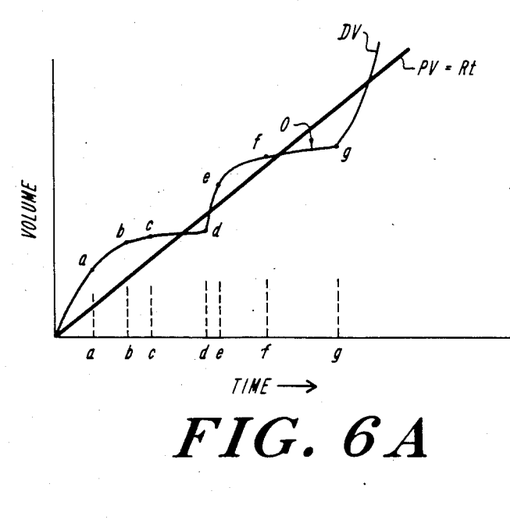

The precise operation of the present controller in effecting flow control, and its distinction from prior devices is illustrated by FIGS. 6 and 6A, which show graphs of the flow rate adjusted by the present device, and the total delivered volume of the system under typical conditions. These figures are analogous to, and presented for comparison with, FIGS. 3 and 3A of the prior art discussed above.

Shown in FIG. 6 is a programmed rate R, which is a constant ideal flow rate corresponding to the user-entered dose and time data. Also shown are a sequence of other constant rates, denoted target rate 1, target rate 2, target rate 3 . . . etc., which are sequentially determined over the course of the infusion. A further constant rate segment "O" is shown, corresponding to an instance of total tube occlusion, when the flow stops. As shown, the target rates may lie above or below the programmed rate. The actual control rate is adjusted by the controller, at any given time, so as to reach the target rate in effect at that time.

The target rate at a given time, which, as discussed below, is derived by the controller pursuant to the operation of its program, is derived with reference to both the cumulative drop count, and the program rate, and is calculated to be a rate which will restore the programmed volume—i.e., minimize the error in actual delivered volume. Thus, as shown in FIG. 6, when the system commences operation at a high rate resulting in excessive delivery, a rate (target rate 1) is calculated less than the programmed rate R which will restore the correct cumulative volume. As shown in the illustration rate graph, FIG. 6, at time b, even though the adjustment has lowered the rate to below the programmed rate R, the delivered volume has not yet caught up with the ideal volume, and a new target rate 2 is calculated. As shown, this calculated target rate 2 is even lower than the actual rate, and as the clamp is closed further down toward this rate, the flow rate drops accordingly. Similarly when at time d the total delivered volume finally falls below the programmed volume, a new target rate 3 is set, slightly above the programmed rate and the clamp is driven to correct the actual drip rate toward target rate 3. At time f, the rate falls to O as a result of occlusion, the discrepancy between actual delivered volume and programmed volume mounts, and it soon becomes necessary to set a higher target rate 4, which is not attained due to continued occlusion. Thereafter an even higher target 5 is set, to which the rate climbs when the tube is no longer pinched at time g. Thereafter, if no serious occlusion occurs, the lost volume is made up, and the target rate again ranges close to the programmed rate. During this series of corrections various alarms are provided to warn of an occluded set, and to initiate appropriate action when the delivered volume cannot be corrected without resorting to an excessive infusion rate.

It will be appreciated that this rat control depicted in FIG. 6, which adjusts the current drip rate to an adaptively defined target rate so as to eliminate long-term volumetric error, offers a significant improvement over the close-tolerance fixed rate controller of the prior art, especially when one or more periods of tube occlusion occur.

In FIG. 6A the resultant delivered volume for the rate curve of FIG. 6 is plotted. As before a straight line shows the ideal or programmed volume PV corresponding to the expected delivered dose, at each instant t for the fixed average delivery rate R. Total delivered volume is indicated by curve DV, which, as the actual average rate is adjusted to the target rate, will approach line PV. Occlusions O, as before, result in a constant, or horizontal portion of the DV curve for the duration of the occlusion, but unlike the case of FIG. 3A, because the target rate is raised to recoup occlusion losses, the total volume reapproaches the programmed curve PV when the occlusion stops, rather than simply tracking below the curve by an amount equal to the missed dose. Thus, in the event further occlusions 02, 03, etc. occur, the volume does not cumulate further errors; rather each error is corrected in time.

The precise operation of the control unit will now be explained with reference to FIG. 4, which shows the logic flow structure of the control program of the device.

As discussed, the controller operates under microprocessor control, and thus, it will be readily appreciated, there is provided a frequency standard which serves as a "clock" for the performance of the operations which will now be discussed The clock is configured as a 24-hour real time clock, and has a timer interrupt 41 effective to provide a signal every $2^{-5}$ seconds. The controller receives drop detection signals and operates upon them under its program in a manner understood in the art, so as to develop representations of values indicative e.g., of the current drop rate and the programmed rate. These representations are stored in a RAM. Thus there will be available at any given time such data, as well as possibly signals from hardware sensors which may indicate, for instance, the occurrence of streaming or an empty reservoir. As shown in FIG. 4, timer interrupt 41 initiates running of a safety subroutine, low rate checker 42, in the control program, operative upon such derived data stored in RAM and on the signals developed by hardware sensors, to signal the occurrence of alarm conditions.

In addition to this periodic polling of alarm conditions, the controller receives a signal upon the occurrence of each falling drop, and each such signal initiates a drop interrupt routine 43 whereby the time interval between that drop and the occurrence of the preceding drop signal is stored for processing. Specifically, because of the variation in timing of the falling drops even at a nominally stable rate of flow can be large, the timing information for each drop is stored in a queue, the length of (i.e., the number entries in) which is a function of the selected flow control rate, and the data for the whole queue is averaged to determine the current drip rate. The present device is designed to maintain delivery rates in the range of 0-300 drops per minute, and it has been found that setting the queue length, denoted QCNT, equal to 2 plus the quotient (rounded to a whole number) of the control rate in drops per minute divided by 30, provides data for a reasonably stable measure of the actual drop rate. Thus, e.g., when the drop rate is under 30 per minute, only two drops need be accumulated; at 300 drops per minute, a dozen drops are accumulated. The control program of the microprocessor initially sets up in RAM, a ring of QCNT addresses, into which are gated the last QCNT drop intervals, which are the basis of a time averaging discussed below in relation to 47 of FIG. 4.

The drop interrupt routine 43 initiates another set of safety checks, namely those of the streaming and the high drip rate checker 44. In the preferred embodiment, a hardware stream detector is provided which, upon occurrence of physical streaming between the reservoir and the lower fluid in the drip chamber, develops a "high" signal. This hardware stream detector may be an optical one, which in an optical drip detector is operative to sense continuous changes in source light intensity in the range of 5% of the nominal light source signal, or it may be, for instance, a static-charge actuated or a capacitatively-coupled electronic sensor. The high rate checker 44 triggers an alarm in the event the streaming detector line is high. In addition, rate check 44 activates an alarm if a drop rate over 400 drops/minute occurs and persists for 5 consecutive drops.

A low rate alarm structure is also incorporated in 42 at this stage of the controller, and includes an occlusion time counter which signals the absence of drops for an adaptively defined "occlusion time" interval which is a function of the drop rate. With the occurrence of each drip detection signal, checker means 42 sets the counter to the "occlusion time," an adaptively defined time interval. The counter then counts down with each signal from timer interrupt 41. In the preferred embodiment, the occlusion time is set to initially be an interval such as 20 or 40 seconds, sufficient to allow an attendant to prime the infusion set. Thereafter, with the next drop signal, the counter is reset to another similarly long interval, as the controller establishes a flow rate. Once several drops have fallen, a flow rate is determined, and the occlusion time counter is reset, in the preferred embodiment, to a time interval of approximately $$\frac{160}{(2^{QCNT} + 6)}$$

seconds, a quantity which will range between approximately 0.2 and 10 seconds. Thereafter, the counter counts down with each signal from timer interrupt 41, and is reset to the adaptively defined "occlusion time" with the occurrence of each drip signal. If the counter reaches a lower threshhold, equal to $(-1)$ seconds in the preferred embodiment, an occlusion signal appears at the output of checker 42. This signal may then activate a user alert beep (in case the tube is pinched) and also a clamp opening control regimen which causes the clamp to open in an attempt to re-establish drip flow. However, because the absence of drip signals may be indiscernible from the occurrence of streaming, a hazardous condition, in the event the occlusion signal persists, the occlusion signal also operates a solenoid-triggered pinch clamp to shut down flow entirely. This pinch clamp, in the preferred embodiment, comprises a plunger mounted within the control housing, downstream from the clamping elements, and positioned so that, when triggered, it protrudes from the housing and captures the flow tube against a face of the removable clamp unit, thereby entirely pinching off the tube, to avert runaway infusion. In this manner, or stored data indicative of commonly occurring alarm conditions is polled during the normal operation of the . controller and suitable alarms actuated if necessary.

Figure 4:
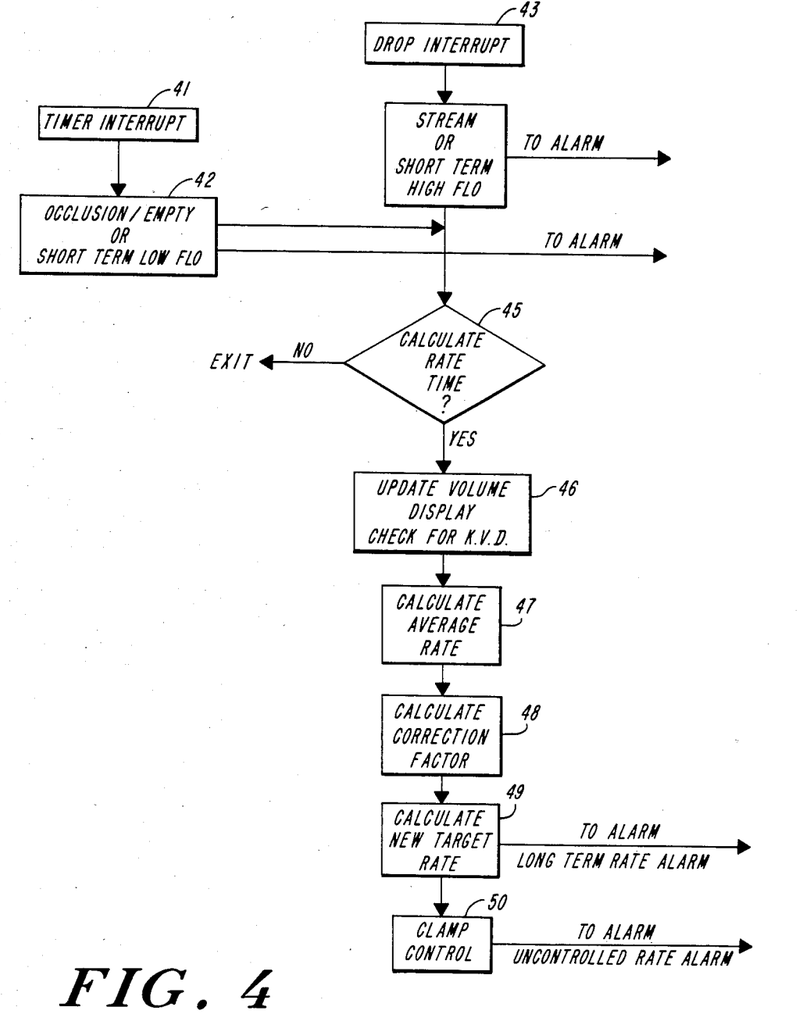
FIG. 4 shows the logic flow structure of the control program of the device.

Referring still to FIG. 4, after the above alarm subroutines have run, a rate time calculation 45 is performed to yield the time (in $2^{-4}$ second units) at which the rate correction algorithm will next be implemented. This is set to be a time, assuming the rate remains regular, when QCNT drops will have occurred. In the prototype embodiment under discussion, this time interval is set to (QCNT-1) times the reciprocal of the current drop control rate. When it is determined that the end of this time interval has been reached, the controller proceeds to the further steps of updating displays and then proceeds to implement its rate control functions. As shown in the logic flow, FIG. 4, at this point, before proceeding, a show, check and proceed routine 46 is evoked. The cumulative delivered volume is displayed and, if the real time has reached the end time previously entered by the user, the present delivery is aborted and delivery is reestablished at a KVO rate, which may be, e.g., 5 drops per minute; otherwise the next control steps are initiated. In the preferred embodiment the cumulative volume is displayed in cc's, and the conversion from drops to cubic centimeters is accomplished via programmed conversion factors within the machine. As a first step in implementing its rate control, a quantity, average rate 47, is set equal to reciprocal of the average of the sum of the intervals between the QCNT drops in the current queue. A second quantity, adjustment factor 48, is set equal to the ratio of the actual delivered volume and the programmed volume. Finally a new target rate 49 is set equal to an amount which, in the preferred embodiment of the invention, varies from the programmed rate by the programmed rate times the adjustment factor. This results in a target rate which will, in an amount of time equal to the elapsed time, "zero out" the accumulated error. In a second and preferred embodiment of the present invention, rather than an adjustment factor ratiometrically derived from the volume ratio, a series of 5 fractional adjustment factors are defined, based upon a range of present status delivered volume errors, called volume tolerance bands in the discussion below, so as to quickly correct for delivery errors without modifying the flow rate too abruptly.

Figure 7:
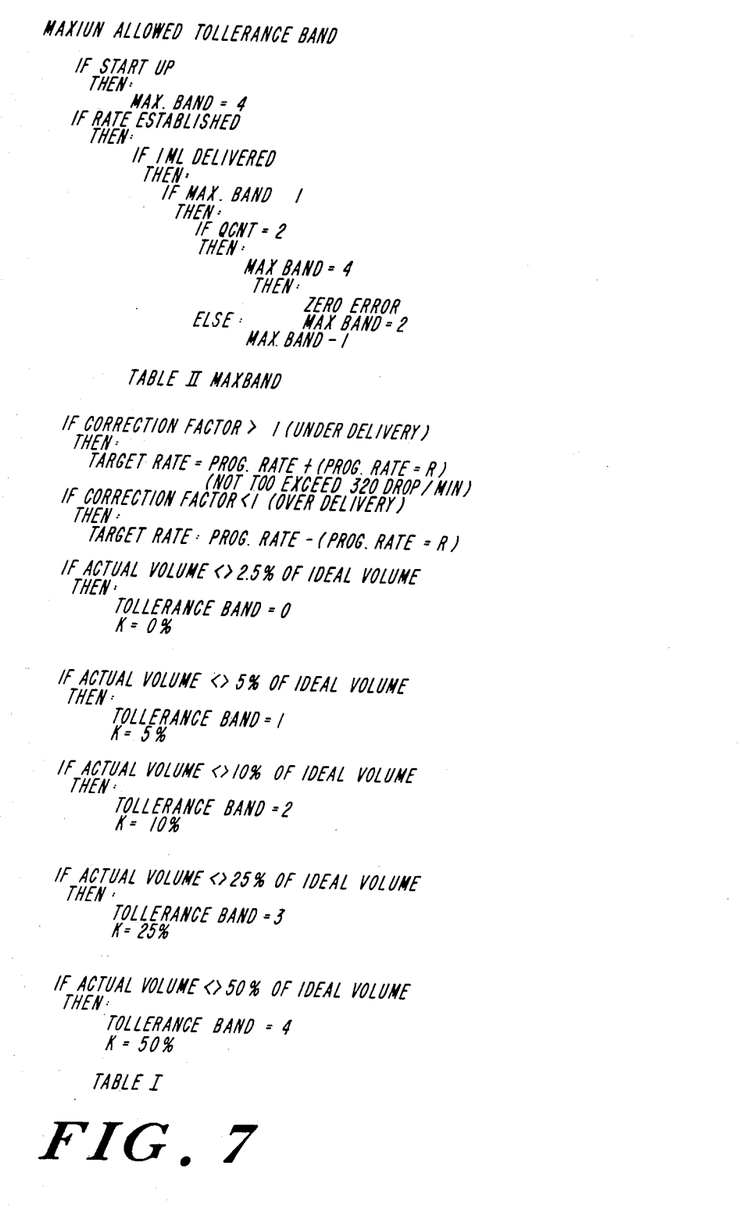
FIG. 7 shows the tolerance bands, and adjustment factors of a preferred embodiment of the controller.

These adjustment factors of the preferred embodiment, and the volume tolerance bands to which they correspond, are set forth in FIG. 7 as table I. Table I of FIG. 7 shows the adjustment K which is adopted for a given tolerance band to set a target rate, as a multiple of $[1+K$ (correction factor)$]R$ so as to correct the delivered volume error, where the term ("correction factor") here simply indicates the sign of the quantity (PV-DV). (R is as defined above in connection with FIG. 6 as a programmed rate.) As shown, the ideal programmed rate is increased (or decreased) stepwise by 0, 5, 10, 25 or 50 percent depending upon the direction and percentage amount of delivered volume error, so as to quickly make up that error. In particular, as soon as the volume error enters the lower limit of a tolerance band (e.g., is above 10%, hence into the 10-to-25% tolerance band), the target rate is set with a factor corresponding to the upper limit of that band (e.g., 25%, here) so as to zero out the delivered volume error. Thus the volume error will, under ordinary delivery circumstances, be promptly controlled so as to fall within progressively narrower tolerance bands as time proceeds.

Nonetheless, in the event tube pinching occurs, adjustment of the clamp may be ineffective to recapture the programmed volume and the delivery error may progress into a greater tolerance band, which would require massive rate corrections to rectify. Furthermore, the attainment of e.g., tolerance band 4 after a protracted delivery time, would, in itself, indicate a prolonged period of grossly erroneous delivery rates or similar condition (e.g., a broken output flow line), a condition which should be communicated to attendant personnel. Accordingly, a maximum permissible tolerance band, denoted MAXBAND, is defined in the control software and the rate calculating means 49 also compares the present tolerance band to the quantity MAXBAND, actuating a long-term rate alarm if the required target rate exceeds MAXBAND. Table II of FIG. 7 sets forth the adaptive definition of MAXBAND. It will be seen that the previously discussed control steps will in general, absent tube occlusion or leakage, diminish the quantity MAXBAND, and that as the delivery progresses, progressively longer instances of occlusion may be accommodated without triggering this alarm condition. Assuming now that the long-term band tolerance MAXBAND is not exceeded, the controller proceeds to adjust the clamp to achieve the target rate by clamp control means 50. This operation will now be discussed in greater detail.

Figure 5:
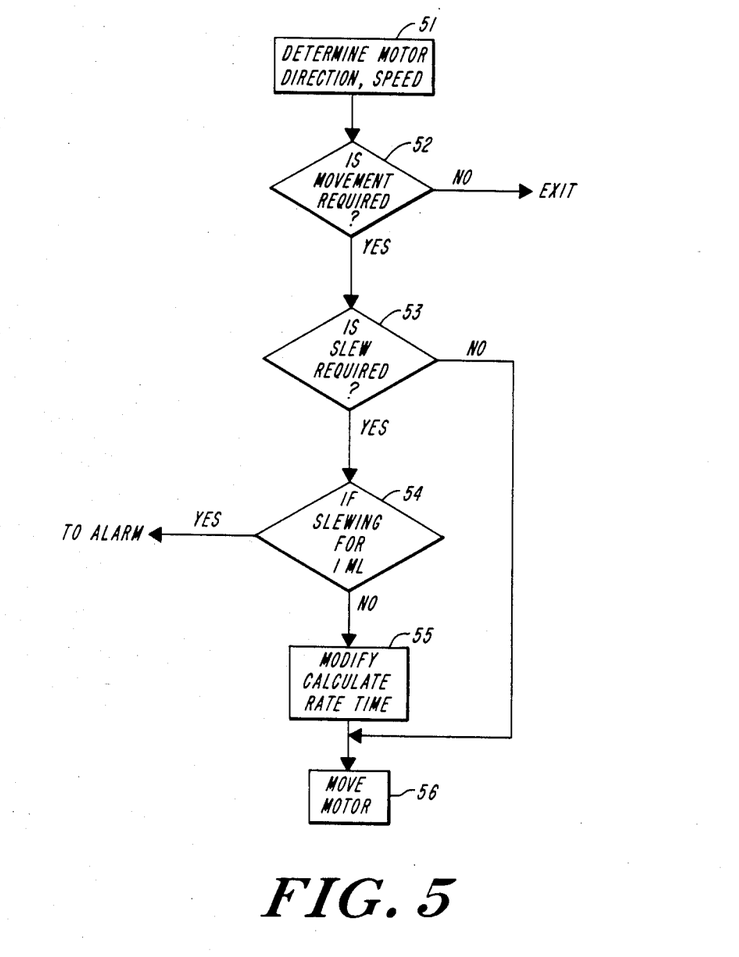
FIG. 5 shows a logic flow chart of the clamp control operation of the present controller.

FIG. 5 shows the logic flow of the clamp control means 50 of the present controller to achieve the rate set by target rate means 49 of FIG. 4. In the preferred embodiment discussed, a clamp system is driven by a bidirectional rotary electric stepping motor, via a meshing gear-like interface, and the clamp is a rotatably adjusted, screw-type clamp; accordingly the control parameters are specified herein in terms such as "motor direction," "slewing" and "speed." It will be appreciated, however, that other methods of incremental clamp control, utilizing, for example, a solenoid driven ratchet clamp are equally amenable to control by the present invention with modifications of a type that would be obvious to one versed in the art, and that control of the direction and speed of such a clamp could be implemented using substantially the same controller.

The first step of clamp control is to determine parameters specifying the direction of motor motion and its speed using clamp parameter determination means 51. In the embodiment discussed, the motor is bidirectional, and may be actuated at any of 5 speeds, with the faster speeds used for the higher flow rates. The motor direction will depend simply on whether the current rate is above or below the current target rate by a threshhold amount. Once the motor parameters are determined, a check 52 of the discrepancy between the actual and the target rate, previously stored, is performed, and if they agree within 5% no motor movement is initiated. Otherwise a comparison means 53 compares these rates and in the event the rate discrepancy is greater than a first threshhold amount, specified in the preferred embodiment as the lesser of QCNT* 8 or 32 drops per minute, then an accelerating adjustment of the clamp, which I call slewing, is undertaken. Otherwise, i.e., if clamp movement is required, but the rate discrepancy is not so great as to require an accelerated repositioning of the clamp, motor actuation 56 in accordance with the parameters determined by the clamp parameter determination means 51 is effected. In that case, the motor which is a stepping motor, is actuated to move at the selected speed in the appropriate direction.

In the event comparison means 53 determines the high rate discrepancy to exist, slewing of the clamp commences and continues until the rate discrepancy falls to within QCNT *4 or 16 drops per minute. Slewing is accomplished as follows. Firstly, as a safety measure, the volume continues to be updated with the occurrence of each falling drop, and when a fixed increment, for example one millilitre, has been delivered, a check of the slew condition 54 is made. If slewing continues (i.e., the rate has not yet been controlled to within QCNT *4 or 16 drops per minute) an alarm is actuated. This check 54 commonly signals conditions such as tube occlusion, failure of integrity of the drip chamber or flow line above the clamp, or other clamp or clamp control system failure. It will be appreciated that during normal operation the entire rate-checking and target-rate-setting operation is usually performed only once every QCNT drops, at the interval determined by the CALCULATE RATE TIME means 45 of the control diagram, FIG. 4.

When the rate error is large and the clamp is being moved, the determination of CALCULATE RATE TIME 45, may, as a practical matter result in too long an interval to allow the flow to proceed uncorrected, or may result in performing the average rate calculation with rate data which are heavily skewed by the ongoing adjustment resulting in over correction of the clamp. Accordingly, during slewing, a modification 55 of the calculated rate time is performed to assure more frequent execution of the target rate setting and flow adjustment steps. In the preferred embodiment, the determination of a new value of CALCULATE RATE TIME of routine 45 is set equal to (old value of CALCULATE RATE TIME/2)+1—i.e., 1/16 second longer than half the previously calculated time interval for initiating the rate check and other calculations. Thus, for large uncontrolled flow discrepancies, as slewing continues, the clamp will be reset at successively shorter intervals of time To prevent the rate setting and clamp movement programs from executing continuously, a lower limit is set for the time interval which is substituted or CALCULATE RATE TIME, at which the rate setting and clamp movement occurs. This limit is ¼ second if the current drop rate is below 30 per minute. For drop rates at and above 30 per minute, this limit is 3/16 second. In this manner a series of one or more brief actuations of the clamp motor is effected to move the clamp in such a way as to achieve the target rate within the operation of a stable control loop based on simple drop rate and cumulative drop count determinations.

It will be appreciated that the present invention in providing a controller for medication infusion which eliminates the cumulation of volumetric errors, or hysteresis, characteristic of rate-based controllers, represents a distinct improvement over the art. In the preferred embodiment utilizing a series of tolerance bands and a small number of correction factors, the entire rate control and alarm structure subsystems may be implemented by simple digital cumulation, comparison, and rounding-off operations, avoiding the need for calculation-intensive arithmetical operations. Thus, the device requires a small instruction set, making it cheaply and safely implemented in a small and autonomous control system using one or more readily available microprocessor chips.

What is claimed is:

1. A medical infusion system for conrolling the flow of fluid from a reservoir through a drip chamber via a flow tube and valve arrangement to a patient, such system comprising:
   data entry means for permitting a user to enter desired dose data;
   data cumulation means, for storing data entered by the user, for receiving drip detection signals derived from a drip detector, and for cumulating such signals to provide a measure of total delivered volume;
   timing means for providing clock signal pulses;
   drip rate analysis means, in communication with the timing means, for receiving drip detection signals derived from a drip detector and determinging the current drip rate therefrom;
   target rate means, in communication with the timing means and the data cumulation means for repeatedly deriving a target rate to correct the delivered volume at a given time to a volume corresponding to the user-entered data, the target rate means further including means for determining a plurality of volume tolerance bands corresponding to successive ranges of the relative difference between the total delivered volume and the desired volume at a given time, and also includes means for determining the target rate as a function of a program rate determined from the user-entered data, such function being distinct for each tolerance band; and
   valve control means, in communication with the the drip rate analysis means and the target rate means, for adjusting the valve so that the current drip rate approaches the target rate.

2. A system according to claim 1, wherein the function of the program rate in each tolerance band is a constant multiple of the program rate in that band.

3. A system according to claim 2, wherein each tolerance band is defined by inner and outer limits, and wherein the constant relating to each such tolerance band is approximately the product of the outer limit of the band and the algebraic sign of the relatively difference.

4. A system according to claim 2, wherein
   (i) the system further includes interval signal means for repeatedly generating a run signal at the end of a modifiable predetermined time interval;
   (ii) the target rate means is in communication with the interval signal means and includes means for deriving a target rate at the end of the predetermined interval; and
   (iii) the system further includes (a) slewing means, for repetitively determining when the current rate differs from the target rate by more than a predetermined amount; and (b) modifying means, in communication with the slewing means and the interval signal means, for modifying the predetermined interval to a shorter interval, subject to a lower limit, each time the slewing means determines that current rate differs from the target rate by more than the predetermined amount.

5. A system according to claim 3, wherein the outer limit of a band is approximately twice the inner limit thereof.

6. A system according to claim 5, including tolerance bands defined by approximate inner and outer limits of relative difference of 0% and 2.5%, 2.5% and 5%, 5% and 10%, 10% and 25%, and 25% and 50%.

7. A system according to claim 1, wherein
   (i) the system further includes interval signal means for repeatedly generating a run signal at the end of a modifiable predetermined time interval;
   (ii) the target rate means is in communication with the interval signal means and includes means for deriving a target rate at the end of the predetermined interval; and
   (iii) the system further includes (a) slewing means, for repetitively determining when the current rate differs from the target rate by more than a predetermined amount; and (b) modifying means, in communication with the slewing means and the interval signal means, for modifying the predetermined interval to a shorter interval, subject to a lower limit, each time the slewing means determines that current rate differs from the target rate by more than the predetermined amount.

8. A medical infusion system for controlling the flow of fluid from a reservoir through a drip chamber via a flow tube and valve arrangement to a patient, such system comprising:
   data entry means for permitting a user to enter desired dose data;
   data cumulation means, for storing data entered by the user, for receiving drip detection signals derived from a drip detector, and for cumulating such signals to provide a measure of total delivered volume, the data cumulation means further comrising queue means, in communication with the timing means, for cumulating data signals representative of the time of occurrence of a predetermined number of consecutive drip detection signals, such predetermined number being a variable increasing function of the magnitude of the drip rate;
   timing means for providing clock signal pulses;
   drip rate analysis means, in communication with the timing means, for receiving drip detection signals derived from a drip detector and determining the current drip rate therefrom, the drip rate analysis means further including means in communication with the queue means for determining the average drip rate of the predetermined number of drops from the data signals in the queue; so that a stable measure of drip rate is provided, irrespective of changes in the relative magnitude of the drip rate;
   target rate means, in communication with the timing means and the data cumulation means for repeatedly deriving a target rate to correct the delivered volume at a given time to a volume corresponding to the user-entered data; and
   valve control means, in communication with the the drip rate analysis means and the target rate means, for adjusting the valve so that the current drip rate approaches the target rate.

9. A system according to claim 8, wherein the predetermined number is approximately equal to $C+[R/30]$, where C is a constant, and R denotes the drip rate in drops per minute and the brackets [] define a step function denoting the greatest integer less than the bracketed quantity.

10. A system according to claim 9, wherein C=2.

11. A system according to claim 8, comprising:
(i) occlusion number means in communication with the drip rate analysis means for repeatedly determining an occlusion number as a function of the current drip rate; and
(ii) resettable occlusion time counter means, in communication with the occlusion number means and the timing means, for decrementing the occlusion number upon each clock signal pulse and for providing an alarm signal when the occlusion number has been decremented to a threshold, such means being reset to a new occlusion number on receipt of a drip detection signal if the alarm signal has not been provided.

12. A system according to claim 11, wherein the occlusion number is inversely proportional to $2^{QCNT}+D$ where QCNT is the predetermined number and D is a constant.

13. A system according to claim 12, wherein D is approximately 6.

14. A medical infusion system for controlling the flow of fluid from a reservoir through a drip chamber via a flow tube and valve arrangement to a patient, such system comprising:

data entry means for permitting a user to enter desired dose data;

data cumulation means, for storing data entered by the user, for receiving drip detection signals derived from a drip detector, and for cumulating such signals to provide a measure of total delivered volume;

timing means for providing clock signal pulses;

drip rate analysis means, in communication with the timing means, for receiving drip detection signals derived from a drip detector and determining the current drip rate therefrom;

target rate means, in communication with the timing means and the data cumulation means for repeatedly deriving a target rate to correct the delivered volume at a given time to a volume corresponding to the user-entered data;

valve control means, in communication with the the drip rate analysis means and the target rate means, for adjusting the valve so that the current drip rate approaches the target rate;

occlusion number means in communication with the drip rate analysis means for repeatedly determining an occlusion number as a function of the current drip rate; and resettable occlusion time counter means, in communication with the occlusion number means and the timing means, for decrementing the occlusion number upon each clock signal pulse and for providing an alarm signal when the occlusion number has been decremented to a threshold, such means being reset to a new occlusion number on receipt of a drip detection signal if the alarm signal has not been provided.

* * * * *